US00PP26316P2

(12) United States Plant Patent
Jack

(10) Patent No.: US PP26,316 P2
(45) Date of Patent: Jan. 19, 2016

(54) ***CHAMELAUCIUM* PLANT NAMED 'SARAH'S DELIGHT'**

(50) Latin Name: ***Chamelaucium* hybrid**
Varietal Denomination: Sarah's Delight

(71) Applicant: Brian Jack, Coorow (AU)

(72) Inventor: Brian Jack, Coorow (AU)

(73) Assignee: WAFEX PTY LTD, Perth (AU)

( * ) Notice: Subject to any disclaimer, the term of this patent is extended or adjusted under 35 U.S.C. 154(b) by 101 days.

(21) Appl. No.: 13/999,207

(22) Filed: Jan. 29, 2014

Related U.S. Application Data

(60) Provisional application No. 61/849,562, filed on Jan. 29, 2013.

(51) Int. Cl.
*A01H 5/02* (2006.01)

(52) U.S. Cl.
USPC ..... Plt./229

(58) Field of Classification Search
USPC ..... Plt./229
See application file for complete search history.

(56) References Cited

PUBLICATIONS

"Exciting Range of New Waxflower Varietes for the Middle East," Gulf Agriculture, Jul.-Aug. 2011, pp. 16-18.*

* cited by examiner

*Primary Examiner* — Susan McCormick Ewoldt
(74) *Attorney, Agent, or Firm* — Penny J. Aguirre

(57) ABSTRACT

A new cultivar of *Chamelaucium*, 'Sarah's Delight' that is characterized by its early blooming, its large vibrant pink flowers with crimson centers, and its red flower buds.

1 Drawing Sheet

Botanical classification: *Chamelaucium* hybrid.
Variety denomination: 'Sarah's Delight'.

BACKGROUND OF THE INVENTION

The present invention relates to a new and distinct cultivar of *Chamelaucium*, botanically of hybrid origin. The new cultivar will be referred to hereafter by its cultivar name, 'Sarah's Delight'. 'Sarah's Delight' is a new cultivar of waxflower, an evergreen shrub grown for use as a landscape plant and is particularly suited for cut flower use.

The Inventor discovered the new cultivar of *Chamelaucium* in July of 2004 as a naturally occurring branch mutation of *Chamelaucium* 'Teina's Delight' (not patented) in a field row at a nursery in Coorow, Australia.

Asexual propagation of the new cultivar was first accomplished by the Inventor by stem cuttings in Coorow, Australia in July of 2004. Asexual propagation by stem cuttings has determined that the characteristics of this cultivar are stable and are reproduced true to type in successive generations.

SUMMARY OF THE INVENTION

The following traits have been repeatedly observed and represent the characteristics of the new cultivar. These attributes in combination distinguish 'Sarah's Delight' as a unique cultivar of *Chamelaucium*.

1. 'Sarah's Delight' exhibits large vibrant pink flowers with crimson centers.
2. 'Sarah's Delight' exhibits red flower buds.
3. 'Sarah's Delight' is early blooming.

The parent of 'Sarah's Delight', 'Teina's Delight', differs from 'Sarah's Delight' in having smaller flowers that are a lighter pink in color and in blooming later. 'Sarah's Delight' can also be compared to the cultivar 'Painted Lady' (U.S. Plant Pat. No. 9,946). 'Painted Lady' is a parent plant of 'Teina's Delight'. 'Painted Lady' differs from 'Sarah's Delight' in having smaller flowers that are lighter pink in color.

BRIEF DESCRIPTION OF THE DRAWINGS

The accompanying colored photographs illustrate the overall appearance and distinct characteristics of the new cultivar. The photographs were taken of a one year-old plant of the new cultivar as grown outdoors in a field in Coorow, Australia.

The photograph in FIG. 1 provides a view of the flowers and flower buds of 'Sarah's Delight'.

Figure 1:
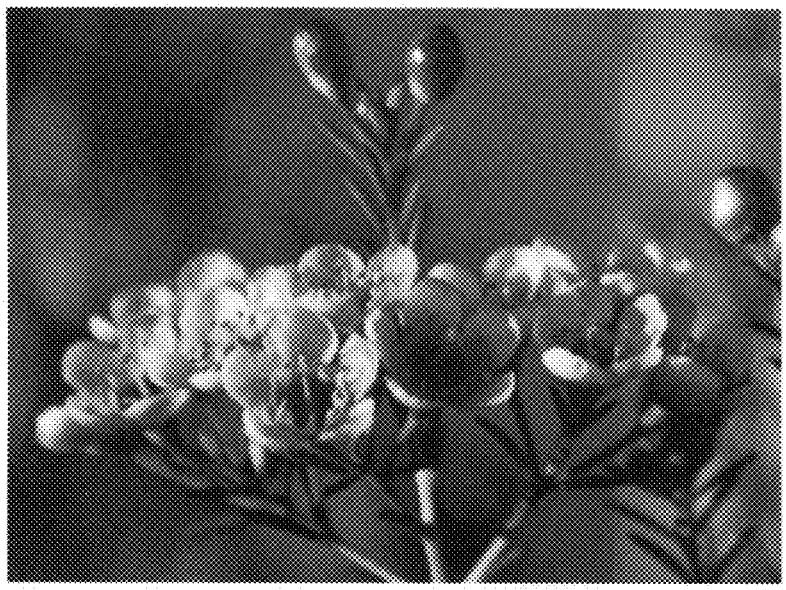
Figure 2:
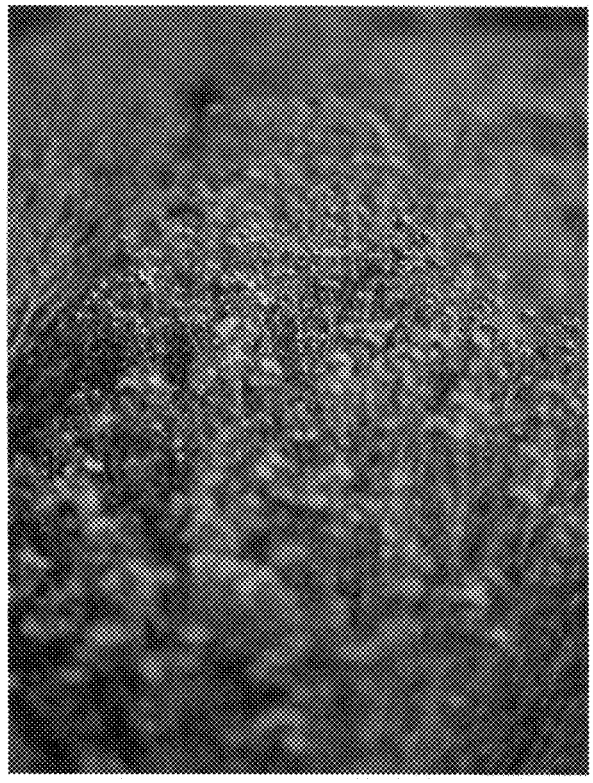

The photograph in FIG. 2 provides a view of a field row of 'Sarah's Delight'.

The colors in the photographs are as close as possible with digital photography techniques available, the color values cited in the detailed botanical description accurately describe the colors of the new *Chamelaucium*.

DETAILED BOTANICAL DESCRIPTION

The following is a detailed description of one year-old plants the new cultivar as grown outdoors in a field in Coorow, Australia. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming habit*.—Blooms for 4 to 6 weeks in early to mid winter in Coorow, Australia.

*Plant type*.—Evergreen shrub.

*Plant habit*.—Upright and semi-open.

*Height and spread*.—1.5 m in height and 1.2 m in spread.

*Hardiness*.—At least in U.S.D.A. Zones 9 to 11.

*Diseases*.—No resistance or susceptibility to diseases has been observed.

*Environmental stresses*.—Grows well in sandy soil, low humidity and hot sun.

*Propagation*.—Stem cuttings.

*Growth*.—Vigorous.

*Roots*.—Strong thick well-branched primary roots with fibrous secondary roots.

*Rooting*.—10 to 20 days in average temperature of 25° to 30° C. in well drained media a greenhouse with rooting hormone (IBA) at 2000 ppm in natural strong light, rooted plant fill a 3-inch tube container in about 60 days in temperatures of 25° C. or above in strong natural light.

Branch description:

*Stem color*.—New growth; 144A and quickly becoming 163D, mature wood; a blend of 166A and 166B.

*Stem surface*.—New growth; glabrous, mature wood; dull, slightly fissured and slightly woolly.

*Branching*.—3 basal branches, up to 20 lateral branches per main stem, an average of 2 Tertiary branches per lateral branch.

*Internode length*.—An average of 3.5 cm in length.

*Stem size*.—Basal branches; average of 3 mm in width and 45 cm in length, lateral branches; up to 15 cm in length and an average of 2 mm in width, tertiary branches; an average of 5 cm in length and 1.5 mm in width.

Foliage description:

*Leaves*.—Simple, linear in shape, opposite arrangement, average of 8 mm in length and 1 mm in width, internode length up to 1 cm, attachment sessile, glabrous on both surfaces, color: new and mature foliage both surfaces; a color between 147A and 147B, slight pine-like fragrance when crushed.

Inflorescence description:

*Inflorescence type*.—Clusters on terminals and upper axils of main stems and lateral and tertiary branches.

*Inflorescence size*.—2.5 cm in length and diameter.

*Inflorescence number*.—Average of 12 per lateral branch.

*Flower number*.—Average of 5 per cluster.

*Flower fragrance*.—None.

*Inflorescence longevity*.—About 5 weeks in the landscape.

*Longevity as a cut flower*.—7 to 12 days.

*Harvest production period for cut flowers*.—Up to 8 weeks.

*Harvest production yield*.—20 to 60 stems on a 2 year-old plant, 70 to 100 stems on plants 3 years old or more.

*Flower type*.—Cup shaped with base of corolla fused to calyx.

*Flower size*.—Average of 1.5 cm in diameter and 1.2 cm in depth.

*Peduncles*.—Average of 1.5 cm in length and 1 mm in diameter, color 144A at apex and 163D at base, surface is dull and smooth.

*Pedicels*.—Average of 8 mm in length and 1.3 mm in diameter, color 144A, surface is glabrous and smooth.

*Flower buds*.—Globose-oblong in shape, an average of 8 mm in length and 6 mm in width, operculum color; N170B to N170D, bud color once operculum sheds; 46A.

*Calyx*.—Campanulate and narrowing to tube (hypanthium), average of 8 mm in length and 1 cm width, including tube portion 4 mm in length and width.

*Sepals*.—5, fused with free obtuse apex, an average of 5 mm in depth and 4 mm in width, margin entire, color of upper and lower surface 144A with free apex 67A to 67C occasionally suffused with 58A, both surfaces are glabrous and waxy.

*Petals*.—5, orbicular in shape, not overlapping, slightly cupped, margin entire, base cuneate to truncate and fused to calyx and nectary, apex is obtuse, average of 7 mm in length width, color of opening flowers upper and lower surface; NN155B suffused with 68A, color of mature flowers; 64B to 64D, surface glabrous and waxy on upper and lower surface.

*Nectaries* (*centers*).—Slightly cupped in shape, 8 mm in diameter and 3 mm in depth, a blend of 146A, 183A, and 17A.

Reproductive organs:

*Pistils*.—1, stigma is an average of 1 mm in diameter, 64A to 64B in color with hairs about 0.5 mm in length, style is an average of 8 cm in length and 0.8 mm in width (narrows at apex) and both 64A and 155A in color, ovary is conical-shaped, 4 mm in length and width and 144A suffused with 58A in color.

*Stamens*.—An average of 10, with 10 infertile stamenoids arranged between stamens, filaments are triangular in shape with a hooked apex, up to 2 mm in length and 1 mm in width and NN155C in color, anthers are an average of 0.5 mm in width and 162D in color, pollen not discernable, stamenoids; triangular in shape, average of 1 mm in length, NN155C with apex 64A in color.

*Fruit and seed*.—Fruit production has not been observed to date.

It is claimed:

1. A new and distinct cultivar *Chamelaucium* plant named 'Sarah's Delight' as herein illustrated and described.

* * * * *